United States Patent
Shabaan et al.

(10) Patent No.: US 12,221,451 B1
(45) Date of Patent: Feb. 11, 2025

(54) DIORGANYL DISELENIDE-CLUBBED QUATERNARY PURINES AS CORROSION INHIBITORS

(71) Applicant: KING FAISAL UNIVERSITY, Al-Ahsa (SA)

(72) Inventors: Saadeldin Elsayed Ibrahim Shabaan, Al-Ahsa (SA); Hany Mohamed Abd El-Lateef Ahmed, Al-Ahsa (SA); Tarek Ahmed Yousef, Riyadh (SA); Ahmed S. M. Aljanabi, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/425,585

(22) Filed: Jan. 29, 2024

Related U.S. Application Data

(62) Division of application No. 18/242,081, filed on Sep. 5, 2023.

(51) Int. Cl.
| | | |
|---|---|---|
| *C07D 487/14* | (2006.01) | |
| *C09D 5/08* | (2006.01) | |
| *C09D 7/63* | (2018.01) | |
| *C23F 11/14* | (2006.01) | |

(52) U.S. Cl.
CPC .......... *C07D 487/14* (2013.01); *C09D 5/086* (2013.01); *C09D 7/63* (2018.01); *C23F 11/149* (2013.01)

(58) Field of Classification Search
None
See application file for complete search history.

(56) References Cited

U.S. PATENT DOCUMENTS

| | | | |
|---|---|---|---|
| 11,851,399 B1 * | 12/2023 | Shabaan | C07C 391/02 |
| 11,920,060 B1 * | 3/2024 | Shaaban | C09D 5/086 |
| 12,006,293 B1 * | 6/2024 | Shaaban | A61K 31/4375 |
| 2014/0155641 A1 * | 6/2014 | Hanes | A61L 27/54 |
| | | | 556/54 |
| 2017/0027168 A1 | 2/2017 | Heath | |

OTHER PUBLICATIONS

Novel tetrazole-based symmetrical diselenides as corrosion inhibitors for N80 carbon steel in 1 M HCl solutions: Experimental and . . . Journal of Molecular Liquids vol. 225, Nov. 2016, pp. 497-508, El-Askalany et al.. (Year: 2016).*

Yang, "Role of Organic and Eco-Friendly Inhibitors on the Corrosion Mitigation of Steel in Acidic Environments-A State-of-Art Review", Molecules 2021, 26(11), 3473.

El-Askalany et al., "Novel tetrazole-based symmetrical diselenides as corrosion inhibitors for N80 carbon steel in 1 M HCl solutions: Experimental and theoretical studies", Journal of Molecular Liquids, vol. 223, Nov. 2016, pp. 497-508.

* cited by examiner

*Primary Examiner* — Joseph D Anthony
(74) *Attorney, Agent, or Firm* — Nath, Goldberg & Meyer; Joshua B. Goldberg

(57) ABSTRACT

New diorganyl diselenide-clubbed quaternary purine are described herein, as well as the use of such diorganyl diselenide compounds in forming anticorrosion coatings for metal. Also described are methods for forming the new diorganyl disleenides compounds as well as anti-corrosion coatings containing the diorganyl disleenides compounds.

7 Claims, 1 Drawing Sheet

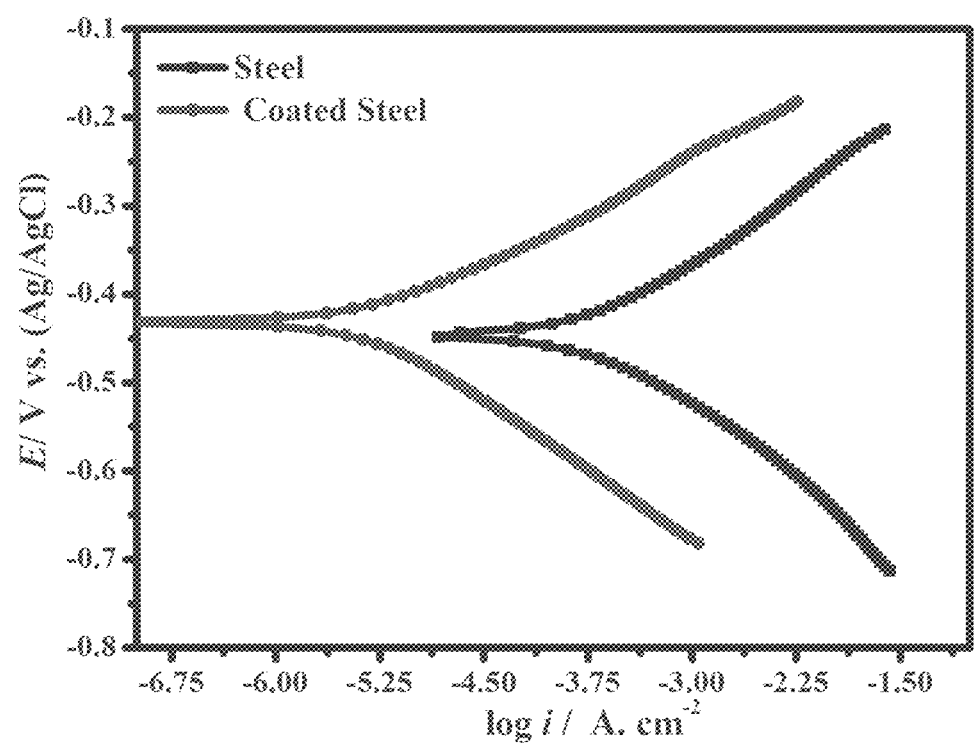

DIORGANYL DISELENIDE-CLUBBED QUATERNARY PURINES AS CORROSION INHIBITORS

CROSS-REFERENCE TO RELATED APPLICATION

This application is a divisional of U.S. patent application Ser. No. 18/242,081, filed on Sep. 5, 2023, the entire contents of which are incorporated herein by reference.

BACKGROUND

1. Field

The disclosure of the present patent application relates to novel diselenide compounds and the use of the same for inhibiting corrosion in metals.

2. Description of the Related Art

Corrosion is a loss of material due to physical, chemical, electro-chemical or biological reaction with the environment. The use of anti-corrosive coatings and linings has become a necessity to safeguard huge investments in terms of money and property. The demand for efficient anti-corrosion coatings is continuously increasing. The anti-corrosive coatings should protect metal surfaces from degradation due to air and moisture oxidation, prevent direct contact of environmental chemical hazards, act as a barrier from corrosive materials, and prolong their structural life and efficiency.

Classical corrosion inhibitors (e.g., organics and inorganics) have shown good inhibition effects. However, their application is limited by their toxicity, high cost, non-degradability, insufficient surface protection, and instability under harsh conditions. On the other hand, green corrosion inhibitors (e.g., surfactant, ionic liquid, natural, and bio-extracts) have attracted the attention of researchers owing to their harmless nature, low-cost, biodegradability, and stability.

A big problem that affects almost everyone is the corrosion of water piping. When materials are exposed to water, chemical reactions between the water and the pipe material have unavoidably resulted in material degradation and corrosion. The variety of materials used, the range in water chemistry considered potable, the variety of strategies to minimize corrosion, and the interaction between these elements all contribute to the complexity of understanding this topic. Despite the intricacy of these systems, pH, alkalinity, and inorganic carbon tend to have the most significant effects on corrosion because they affect the dissolution rates and the stability of formed protective films and scales.

Conventional corrosion inhibitors can function only at room temperature and dilute acid concentration; however, they cannot withstand harsh conditions, i.e., high temperature and concentrated acid (>15 wt. % HCl), required for pipeline cleaning solutions and acidizing fluids, as well as in the petrochemical industries.

Therefore, developing novel corrosion inhibitors solving the aforementioned problems are highly desired.

SUMMARY

The present subject matter relates to the protection of water piping against corrosion using diorganyl diselenide-clubbed quaternary purines. Described herein are products and methods for corrosion protection with eco-friendly, less expensive diorganyl diselenides-clubbed quaternary purines.

In an embodiment, the present subject matter relates to diorganyl diselenides-clubbed quaternary purines of the formula I:

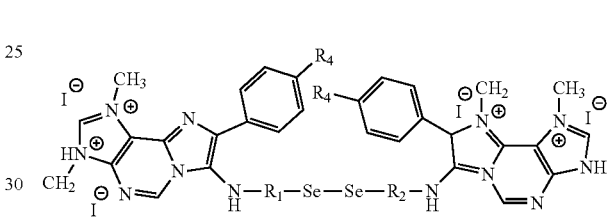

wherein:
R$_1$ and R$_2$ are independently selected from the group consisting of C$_2$-C$_3$ alkyl and

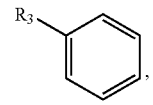

R$_3$ is selected from the group consisting of H, COOMe, and COOEt, and
R$_4$ is selected from the group consisting of hydrogen, 4-NO$_2$—C$_6$H$_4$, 4-F$_2$—C$_6$H$_4$, and 4-MeO—C$_6$H$_4$.

In another embodiment, the present subject matter relates to an anticorrosion coating comprising the diorganyl diselenides compounds described herein.

In a further embodiment, the present subject matter relates to a diorganyl diselenides-clubbed quaternary purine selected from the group consisting of

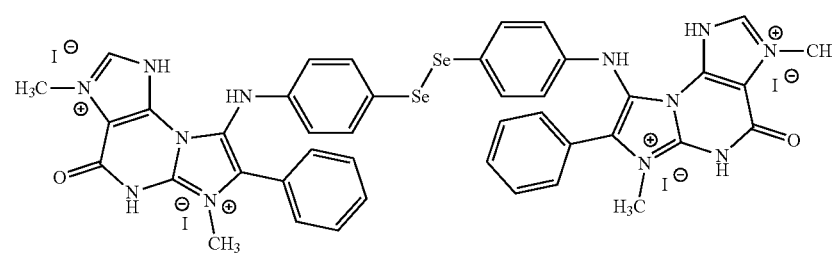

-continued
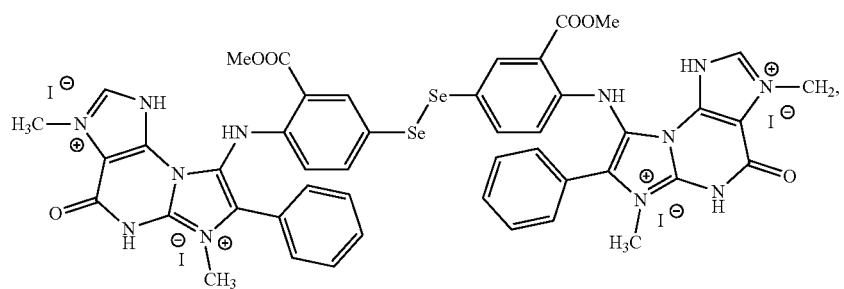
II
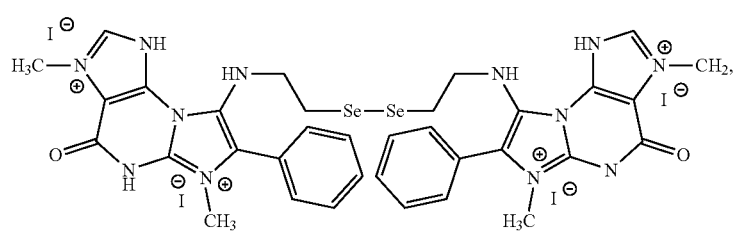
III
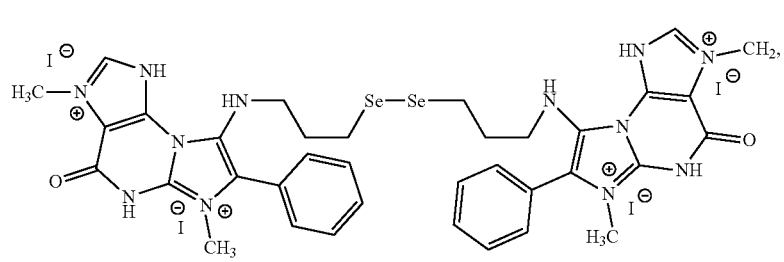
IV
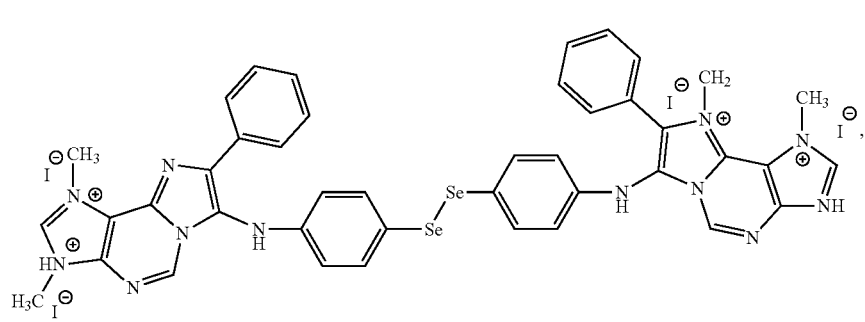
V
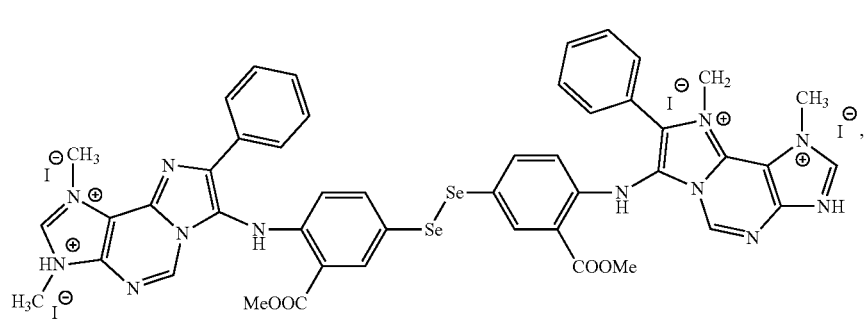
VI

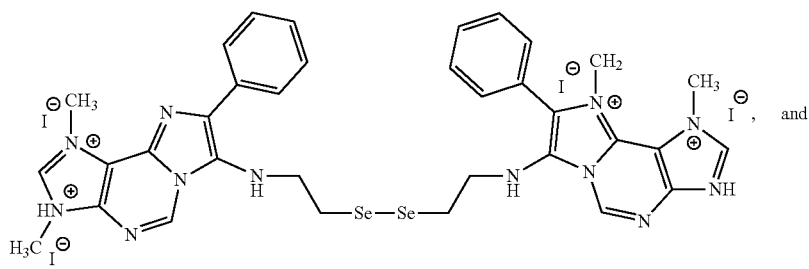

VII

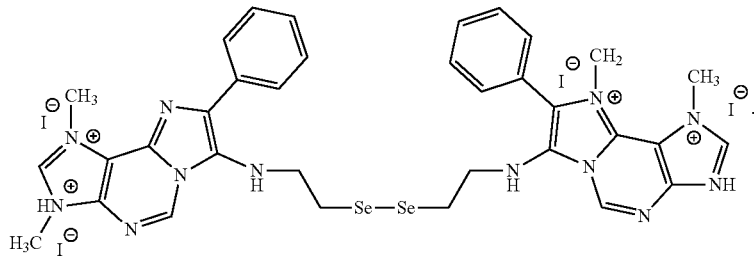

VII

In an additional embodiment, the present subject matter relates to a method of making diorganyl diselenide-clubbed quaternary purine as described herein, using a Groebke-Blackburn-Bienaymé reaction (GBBR) involving the 2-amidine functionality of adenine or guanine. The method can include preparing a solution including a guanine base, benzaldehyde, and dimethylsulfoxide (DMSO); and adding zirconium (IV) chloride and a diselenide compound to the solution to provide the diorganyl diselenide-clubbed quaternary purine in the solution.

These and other features of the present subject matter will become readily apparent upon further review of the following specification.

BRIEF DESCRIPTION OF DRAWINGS

FIG. 1 is a graph showing Tafel plots obtained for the corrosion behavior of uncoated and coated steel in a 3.5% saline solution at 25° C.

Similar reference characters denote corresponding features consistently throughout the attached drawings.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to the protection of metal against corrosion using diorganyl diselenide-clubbed quaternary purines. Described herein are products and methods for corrosion protection of metal which are eco-friendly and economical. Further, unlike many conventional corrosion inhibitors, the present compounds can function efficiently at high temperatures and acid concentration, e.g., >15 wt. % HCl. Accordingly, various aspects of the present subject matter relate to the application of the diorganyl diselenide-clubbed quaternary purines on the surface of metal. The diorganyl diselenide-clubbed quaternary purines can be self-healing. For example, the diorganyl diselenide-clubbed quaternary purines can sense and repair sustained damage to the metal.

In an embodiment, the present subject matter relates to diorganyl diselenide-clubbed quaternary purines of the formula I:

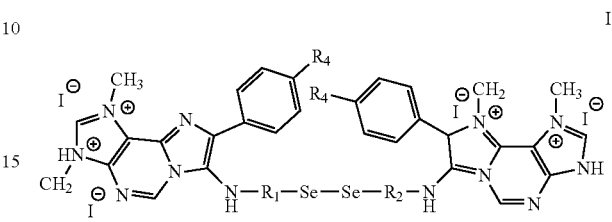

wherein:
R$_1$ and R$_2$ are independently selected from the group consisting of C$_2$-C$_3$ alkyl and

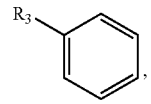

R$_3$ is selected from the group consisting of H, COOMe, and COOEt, and
R$_4$ is selected from the group consisting of hydrogen, 4-NO$_2$—C$_6$H$_4$, 4-F$_2$—C$_6$H$_4$, and 4-MeO—C$_6$H$_4$.

In an embodiment, the diorganyl diselenide-clubbed quaternary purines can be selected from the group consisting of:

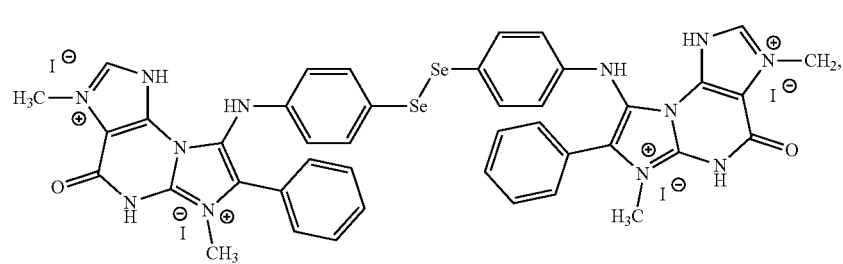

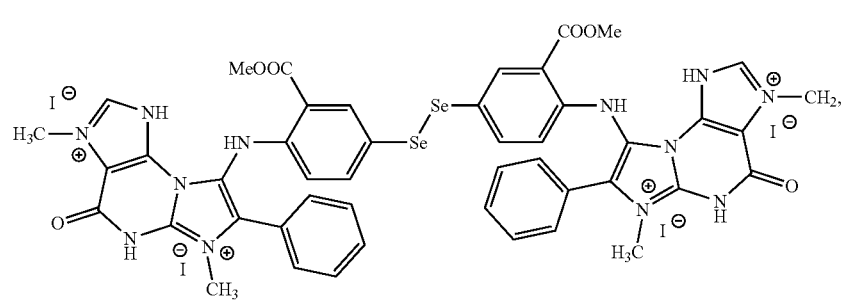

III
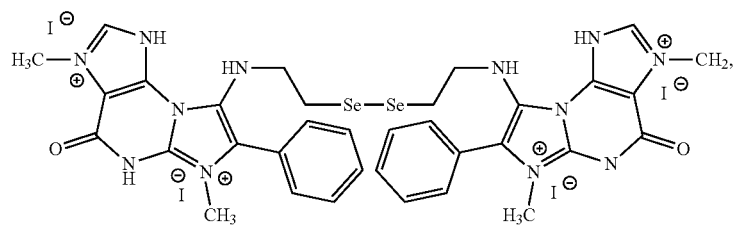
IV
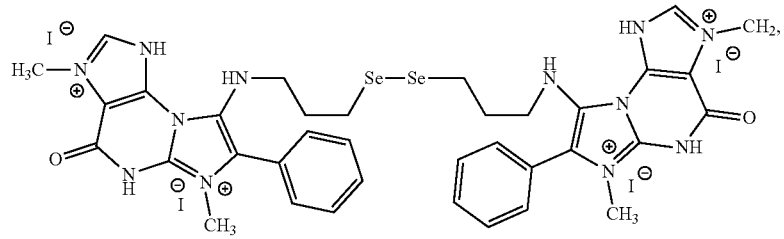
V
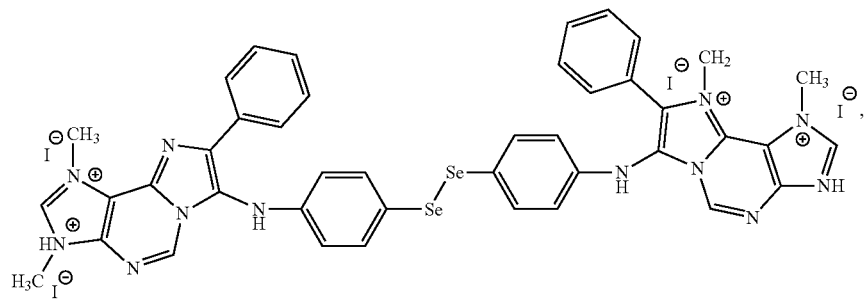
VI
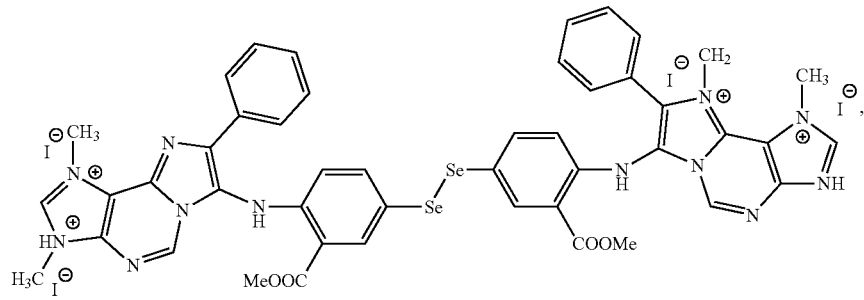
VII, and
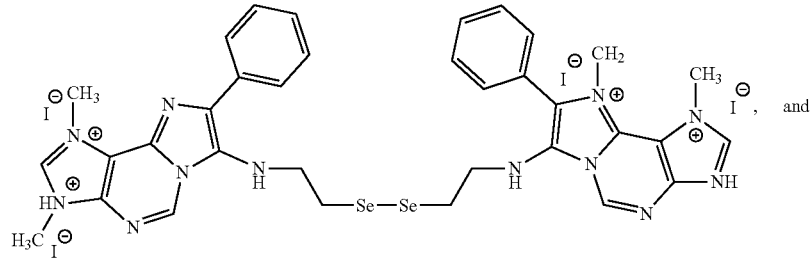
VII
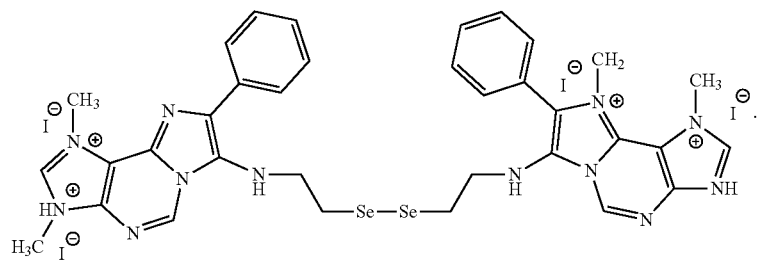

In another embodiment, the present subject matter relates to an anticorrosion coating comprising the diorganyl diselenide-clubbed quaternary purines described herein. In certain embodiments, the anticorrosion coating can be applied to a surface of a metal to form a self-healing diorganyl diselenides layer on the metal, wherein the metal is selected from the group consisting of steel, steel alloy, iron, copper, and a combination thereof. In an embodiment, steel alloy includes nickel, carbon, chromium, manganese, magnesium, silicon, and iron.

In an embodiment, the anticorrosion coating can be applied to a surface of a water pipe formed from the metal.

functionality of a purine base. In an embodiment, the reaction includes preparing a solution including a purine base and benzaldehyde, adding zirconium (IV) chloride and a diselenide compound to the solution to provide the diorganyl diselenide compound, as shown in Scheme 1. In an embodiment, the solution is stirred at a temperature of about 70° C. after the diorganyl diselenide compound is added to the solution. In an embodiment, the purine base is selected from the group consisting of adenine and guanine. In an embodiment, the diselenide compound is selected from the group consisting of 1,2-bis(4-isocyanophenyl) diselane and dimethyl 5,5'-diselanediylbis(2-isocyanobenzoate).

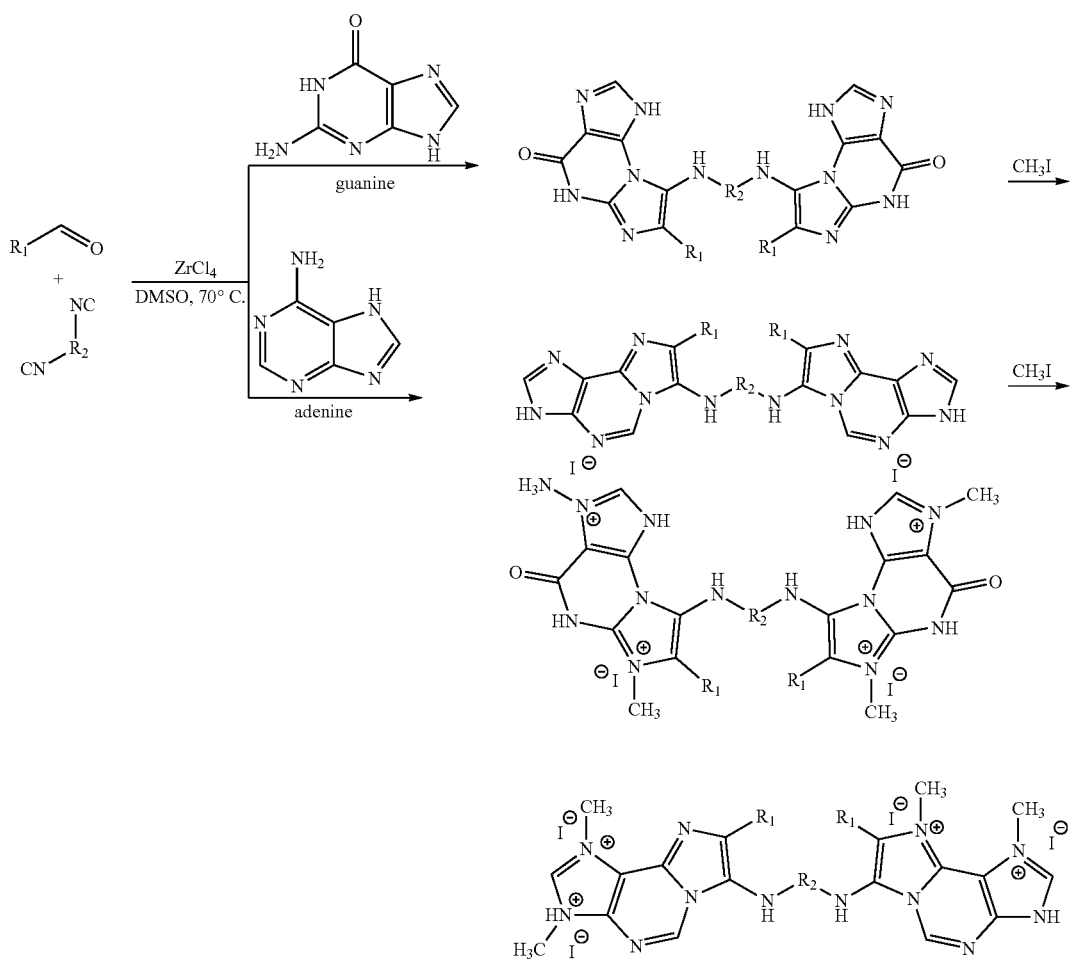

It is believed that cationic ammonium salts of nitrogen-based heterocycles, such as purine, can serve as ideal adsorption sites to prevent corrosion of water pipes because these compounds share free electrons with the metal template. The hydrophobic inhibitor compounds can protect the metals from acid corrosion by protecting the contact surface area available with hydrogen ions ($H^+$). The diselenide bond can offer self-healing and re-processability performance. The diorganyl diselenide tethered quaternary purine can be self-healing and serve as dual corrosion inhibitors.

In another embodiment, the anticorrosion coating can be formed as a homogenous film.

In an additional embodiment, a method of making the diorganyl diselenide compound includes a Groebke-Blackburn-Bienaymé reaction (GBBR) implicating the 2-amidine R1 = $C_6H_5$, 4-$NO_2$-$C_6H_4$, 4-$F_2$-$C_6H_4$, 4-MeO-$C_8$-$H_4$]

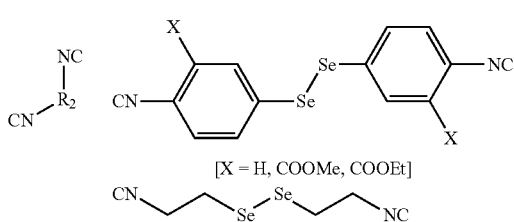

[X = H, COOMe, COOEt]

-continued

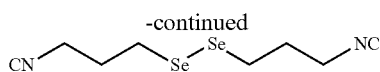

In one embodiment, a method of making the diorganyl diselenides compound as described herein, includes preparing a first solution including guanine, benzaldehyde, and dimethylsulfoxide (DMSO), adding 1,2-bis(4-isocyanophenyl) diselane (1) and $ZrCl_4$ to the first solution to provide a second solution, stirring the second solution, at least partially evaporating the dimethylsulfoxide (DMSO) from the second solution to provide a crude product, and purifying the crude product to provide 8,8'-((diselanediylbis(4,1-phenylene))bis(azanediyl))bis(7-phenyl-1H-imidazo [2,1-b]purin-4 (5H)-one) (2). The iodide salt (3) can be prepared by preparing a solution of (2) in DMF, and adding $CH_3I$ (7 ml) to the solution to provide a reaction mixture. The reaction mixture can be treated with dry diethyl ether to provide (3).

In an embodiment, purifying the crude product can include subjecting the second solution to rotary evaporation under reduced pressure (2 mm Hg) at a temperature ranging from about 50° C. to about 60° C.

This process can be further summarized according to the following Scheme 2:

In another embodiment, a method of making the diorganyl diselenide compound as described herein, includes preparing a first solution including guanine, benzaldehyde, and dimethylsulfoxide (DMSO), adding dimethyl 5,5'-diselanediylbis(2-isocyanobenzoate) (4) (0.17 g, 2 mmol) and $ZrCl_4$ (10 mol %) to the first solution to provide a second solution, stirring the second solution, at least partially evaporating the dimethylsulfoxide (DMSO) from the second solution to provide a crude product, and purifying the crude product to provide dimethyl 5,5'-diselanediylbis(2-((4-oxo-7-phenyl-4,5-dihydro-1H-imidazo [2,1-b]purin-8-yl)amino) benzoate) (5).

In an embodiment, purifying the crude product can include subjecting the second solution to rotary evaporation under reduced pressure (2 mm Hg) at a temperature ranging from about 50° C. to about 60° C. To prepare the purinium iodide salt (6), a solution of (5) (0.01 mol) in DMF (15 ml), $CH_3I$ (7 ml) is added and the reaction mixture is left over night at room temperature. Upon treating the reaction mixture with dry diethyl ether, a precipitate is obtained representing 6.

Scheme 2

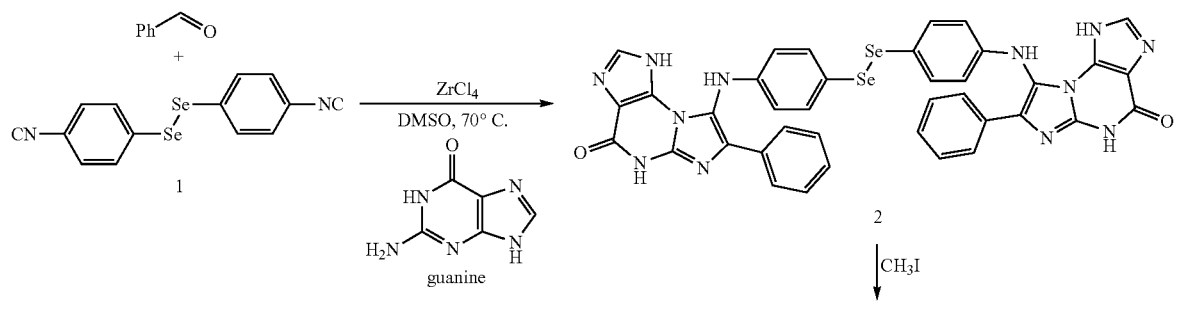

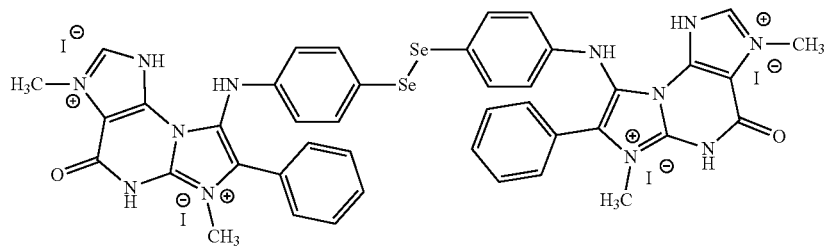

This process can be further summarized according to the following Scheme 3:

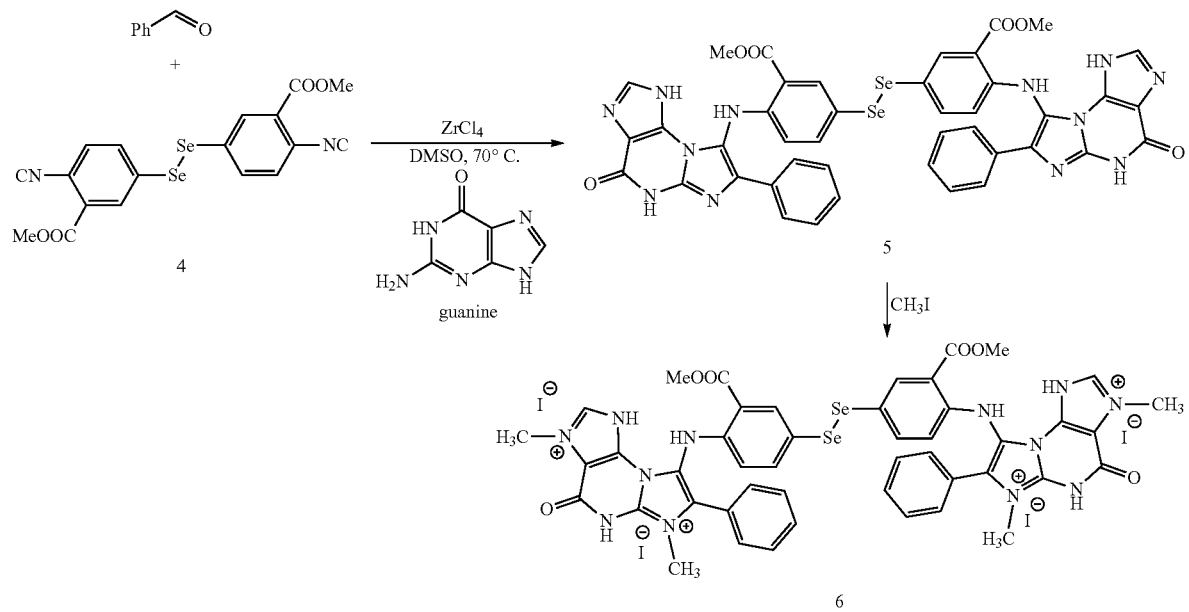

The present teachings are illustrated by the following examples.

EXAMPLES

Example 1

Preparation of Diorganyl Diselenide-Clubbed Quaternary Purine (3)

The diorganyl diselenide-clubbed quaternary purine (3) was prepared as follows and summarized in reaction Scheme 1. To a mixture of guanine (2 mmol) and benzaldehyde (2 mmol) in dimethylsulfoxide (DMSO) (5 mL), 1,2-bis(4-isocyanophenyl) diselane (1) (0.17 g, 2 mmol) and ZrCl$_4$ (10 mol %) were added. The mixture was allowed to stir at 70° C. under open air. After 10 hrs of reaction (monitored by TLC), dimethylsulfoxide (DMSO) was partially removed from the resultant mixture by rotary evaporation under reduced pressure (2 mm Hg) at 50-60° C. (water bath temperature). The direct column chromatographic purification of crude product over silica gel (mesh size: 60-120) eluting with EtOAc-hexane afforded 8,8'-((diselanediylbis (4,1-phenylene))bis(azanediyl))bis(7-phenyl-1H-imidazo [2,1-b]purin-4 (5H)-one) (2). The iodide salt (3) was prepared as follows. To a solution of (2) (0.01 mol) in DMF (15 ml), CH$_3$I (7 ml) was added and the reaction mixture was left over night at room temperature. Upon treating the reaction mixture with dry diethyl ether, a precipitate was obtained representing (3).

Example 2

Preparation of Diorganyl Diselenide-Clubbed Quaternary Purine (6).

The diorganyl diselenide-clubbed quaternary purine (6) was prepared as follows and summarized in Scheme 3. To a mixture of guanine (2 mmol) and benzaldehyde (2 mmol) in dimethylsulfoxide (DMSO) (5 mL), dimethyl 5,5'-diselanediylbis(2-isocyanobenzoate) (4) (0.17 g, 2 mmol) and ZrCl$_4$ (10 mol %) were added. The mixture was allowed to stir at 70° C. under open air. After 10 hrs of reaction (monitored by TLC), dimethylsulfoxide (DMSO) was partially removed from the resultant mixture by rotary evaporation under reduced pressure (2 mm Hg) at 50° C.-60° C. (water bath temperature). The direct column chromatographic purification of crude product over silica gel (mesh size: 60-120) eluting with EtOAc-hexane afforded dimethyl 5,5'-diselanediylbis(2-((4-oxo-7-phenyl-4,5-dihydro-1H-imidazo [2,1-b]purin-8-yl)amino)benzoate) (5). The purinium iodide salt 6 was prepared as follows. To a solution of 5 (0.01 mol) in DMF (15 ml), CH$_3$I (7 ml) was added and the reaction mixture was left over night at room temperature. Upon treating the reaction mixture with dry diethyl ether, a precipitate was obtained representing 6.

Example 3

Electrochemical and Corrosion Inhibition Procedures

Three electrode arrangements were used to conduct electrochemical tests on the carbon steel working electrode. The reference electrode was an Ag/AgCl saturated KCl electrode, while the counter electrode was a Pt wire of 2 mm thickness. A 3.5% saline solution was used as a corrosive medium. Gamry's Potentiostat/Galvanostat/ZRA framework was used to accomplish electrochemical and corrosion inhibition processes. To control the steady state of the open-circuit potential (EOCP), the steel electrode was immersed in the corrosive liquid for 40 minutes prior to the corrosion measurements. Potentiodynamic Polarization (PDP) experiments were conducted at the observed temperature with potentials ranging from −250 mV to +250 mV and a sweep rate of 0.2 mVs$^{-1}$.

Example 4

Potentiodynamic Polarization (PDP) Measurements

For the PDP experiments, steel alloy specimens with the following chemical compositions (in wt %) were used: Nickel (0.014), Carbon (0.073), Chromium (0.05), Manganese (0.18), Magnesium (0.31), Silicon (0.035), and iron (remaining). A mirror polish was achieved on the steel alloy surface by abrading it with emery paper of grades 600 to 2000, followed by bi-distilled water washing and acetone degreasing.

FIG. 1 displays the Tafel plots obtained through the potentiodynamic polarization technique, which were used to investigate the corrosion behavior of steel in a 3.5% saline solution. The experiments were conducted under various conditions, including blank steel and coating with the diorganyl diselenide-clubbed quaternary purines.

The Tafel plots provide a graphical representation of the corrosion rate as a function of the applied potential. The plots show the anodic and cathodic polarization curves, which are used to determine the corrosion potential and corrosion current density of the steel in each solution. The plots clearly demonstrate that the coated film had an impact on the polarized curves. A significant decrease in the rate of both anodic and cathodic reactions was evident from a comparison of the blank steel and coated film curves. However, the anodic reactions were more significantly affected by the presence of the coated film than the cathodic reactions. Although both anodic and cathodic reactions showed a reduction in corrosion, the anodic reactions, which indicate steel dissolution, were more inhibited. The parallel polarization curves confirm that the presence of coated film did not alter the corrosion reaction pathway.

Consequently, the presence of diorganyl diselenide-clubbed quaternary purines film results in a significant reduction in the corrosion current ($i_{cor}$), with the lowest values obtained for the film (22.9 µAcm$^{-2}$) compared to uncoated steel (1326.4 µAcm−2). The protective ability ($\eta_P/\%$) was intended from $i_{cor}$ as per the following Eqn.

$$\eta_P/\% = \left(\frac{i_{cor}^0 - i_{cor}^j}{i_{cor}^0}\right) \times 100 = \theta \times 100 \quad (1)$$

$i_{cor}^0$=corrosion current density of the blank steel, $i_{cor}^i$=corrosion current density of coated steel. The protective ability of the film from the PDP measurements was found to be 98.27%.

It is to be understood that the compounds, coatings, and methods are not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of making a diorganyl diselenide-clubbed quaternary purine having a formula I:

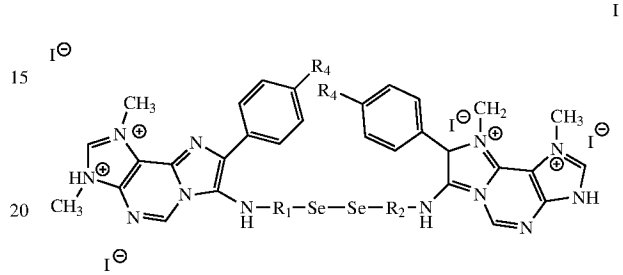

wherein:

R$_1$ and R$_2$ are independently selected from the group consisting of C$_2$-C$_3$ alkyl and

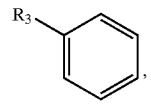

R$_3$ is selected from the group consisting of H, COOMe, and COOEt, and

R$_4$ is selected from the group consisting of hydrogen, 4-NO$_2$—C$_6$H$_4$, 4-F$_2$—C$_6$H$_4$, and 4-MeO—C$_6$H$_4$;

the method comprising:

combining a guanine base, benzaldehyde, and dimethylsulfoxide (DMSO) to provide a solution;

adding methyl iodide to the solution; and adding zirconium (IV) chloride and a diselenide compound to the solution to provide the diorganyl diselenide-clubbed quaternary purine in the solution.

2. The method of claim 1, wherein the solution is stirred at temperature of about 70° C. after the diselenide compound is added to the solution.

3. The method of claim 2, wherein the diorganyl diselenide-clubbed quaternary purine is selected from the group consisting of 1,2-bis(4-isocyanophenyl) diselane and dimethyl 5,5'-diselanediylbis(2-isocyanobenzoate).

4. A method of making a diorganyl diselenide-clubbed quaternary purine of selected from the group consisting of:
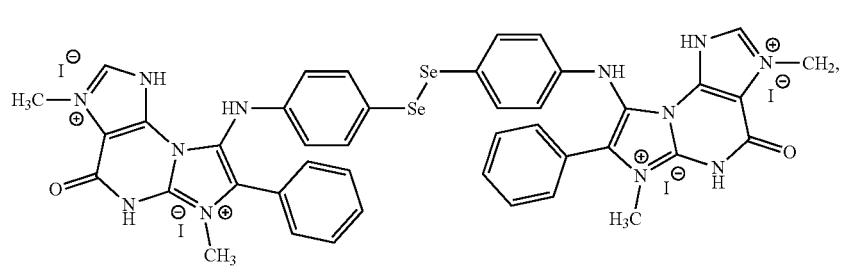
I
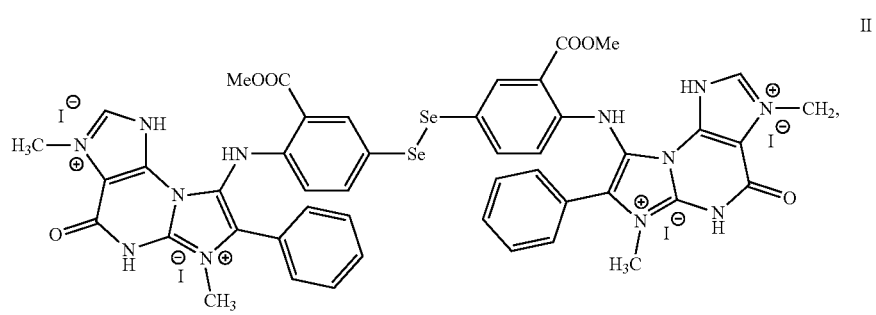
II
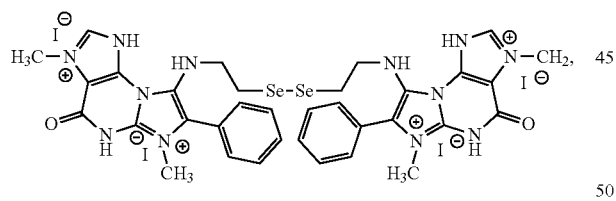
III
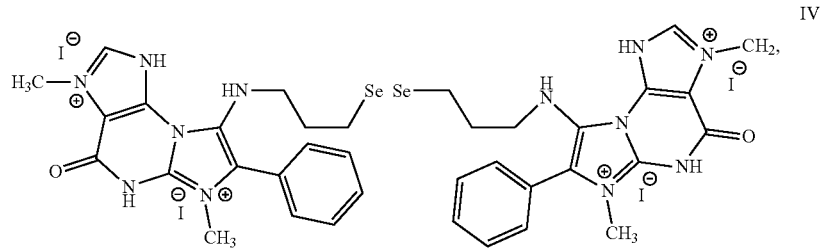
IV

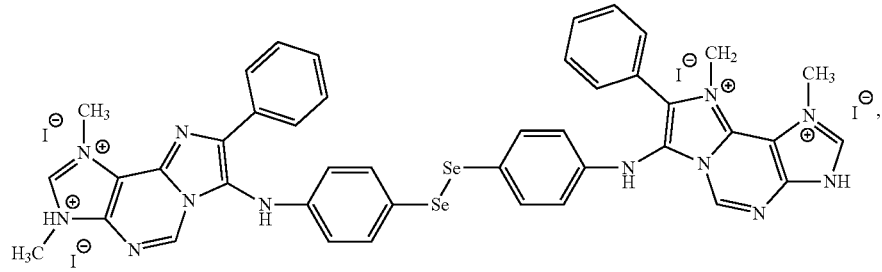

V

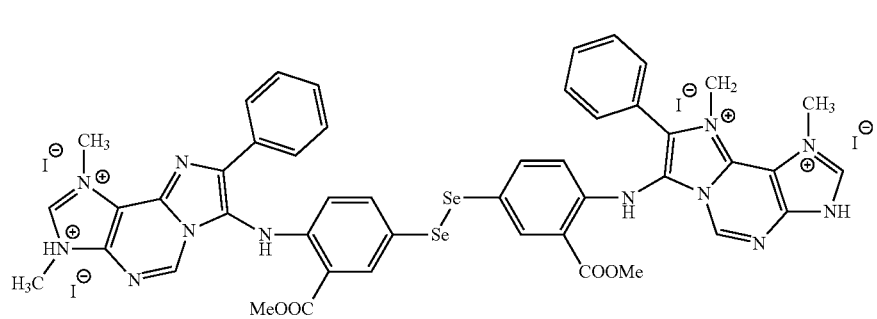

VI

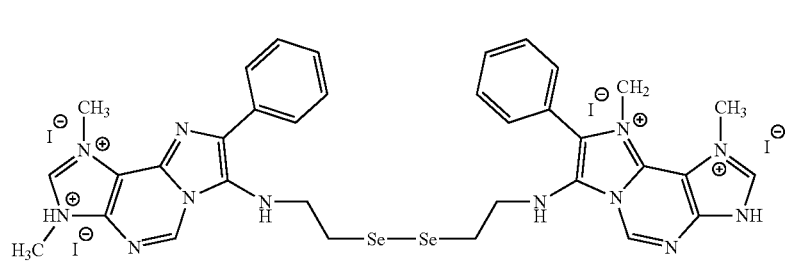

VII and

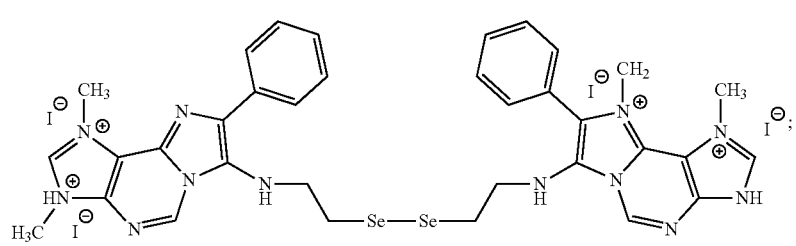

VII the method comprising:
preparing a mixture including guanine and benzaldehyde;
adding the mixture to zirconium (IV) chloride in dimethylsulfoxide (DMSO) to provide a solution;
adding methyl iodide to the solution; and
adding a diselenide compound to the solution to provide the diorganyl diselenide-clubbed quaternary purine.

5. The method of claim 4, wherein the diorganyl diselenide-clubbed quaternary purine is selected from the group consisting of 1,2-bis(4-isocyanophenyl) diselane and dimethyl 5,5'-diselanediylbis(2-isocyanobenzoate).

6. The method of claim 4, wherein the mixture is stirred at temperature of about 70° C.

7. A method of making a diorganyl diselenide-clubbed quaternary purine, comprising:
- preparing a solution including a guanine base, benzaldehyde, and dimethylsulfoxide (DMSO);
- adding methyl iodide to the solution; and
- adding zirconium (IV) chloride and a diselenide compound to the solution to provide the diorganyl diselenide-clubbed quaternary purine in the solution;
- wherein the diorganyl diselenide-clubbed quaternary purine is selected from the group consisting of 1,2-bis (4-isocyanophenyl) diselane and dimethyl 5,5'-diselanediylbis(2-isocyanobenzoate).

* * * * *